United States Patent
van Egmond et al.

(10) Patent No.: US 8,309,776 B2
(45) Date of Patent: Nov. 13, 2012

(54) METHOD FOR CONTAMINANTS REMOVAL IN THE OLEFIN PRODUCTION PROCESS

(75) Inventors: Cornelis F. van Egmond, Pasadena, TX (US); David J. Wilson, Rushden (GB)

(73) Assignee: Stone & Webster Process Technology, Inc., Houston, TX (US)

( * ) Notice: Subject to any disclaimer, the term of this patent is extended or adjusted under 35 U.S.C. 154(b) by 475 days.

(21) Appl. No.: 12/638,170

(22) Filed: Dec. 15, 2009

(65) Prior Publication Data
US 2011/0144397 A1    Jun. 16, 2011

(51) Int. Cl.
*C07C 7/167* (2006.01)
*C07C 7/163* (2006.01)

(52) U.S. Cl. ........ 585/261; 585/262; 585/802; 585/809; 585/810

(58) Field of Classification Search ............... 585/261, 585/262, 802, 809, 810
See application file for complete search history.

(56) References Cited

U.S. PATENT DOCUMENTS

| | | |
|---|---|---|
| 2,582,068 A | 1/1952 | Roberts |
| 3,407,789 A | 10/1968 | Hallee et al. |
| 3,647,682 A | 3/1972 | Rabo et al. |
| 3,649,525 A | 3/1972 | Hilfman |
| 3,758,403 A | 9/1973 | Rosinski et al. |
| 3,820,955 A | 6/1974 | Woebcke |
| 4,002,042 A | 1/1977 | Pryor et al. |
| 4,270,940 A | 6/1981 | Rowles et al. |
| 4,499,055 A | 2/1985 | DiNicolantonio |
| 4,519,825 A | 5/1985 | Bernhard et al. |
| 4,657,571 A | 4/1987 | Gazzi |
| 4,732,598 A | 3/1988 | Rowles et al. |
| 4,814,067 A | 3/1989 | Gartside et al. |
| 4,828,679 A | 5/1989 | Cormier et al. |
| 4,900,347 A | 2/1990 | McCue et al. |
| 4,980,053 A | 12/1990 | Li et al. |
| 5,035,732 A | 7/1991 | McCue, Jr. |
| 5,326,465 A | 7/1994 | Yongqing et al. |
| 5,414,170 A | 5/1995 | McCue et al. |
| 5,859,304 A | 1/1999 | Barchas et al. |
| 6,303,839 B1 | 10/2001 | Marker |
| 6,482,999 B2 | 11/2002 | Fung et al. |
| 6,613,951 B1 | 9/2003 | Brown et al. |
| 7,030,284 B2 | 4/2006 | Shutt |
| 2006/0135828 A1 | 6/2006 | Shutt |

OTHER PUBLICATIONS

UOP/HYDRO MTO Process Methanol to Olefins Conversion. Online publication from UOP LLC, Des Plaines, IL, copyright 2004. <http://www.uop.com/objects/MTO.pdf> (last accessed Mar. 30, 2010).
UOP Technology & More Oct. 2005 Newsletter from UOP LLC, Des Plaines, IL, copyright 2005. <http://www.uop.com/objects/UOPTechMoreOct2005.pdf> (last accessed Mar. 30, 2010). S.H. Lee in "Partial catalytic hydrogenation of acetylene in ethylene production" published on kolmetz.com. <http://kolmetz.com/Article-039.htm> (last accessed Mar. 30, 2010).

*Primary Examiner* — Thuan D Dang
(74) *Attorney, Agent, or Firm* — Locke Lord LLP; Alan B. Clement; Peter J. Fallon

(57) ABSTRACT

The present invention provides a method and reactor system for hydrogenating acetylenes present in the olefin stream derived from the following streams, alone or in combination: petroleum catalytic cracking process and/or oxygenate-to-olefin reactor, such as methanol-to-olefin (MTO) reactor, in an olefin production plant before the distillation steps, wherein the acetylene hydrogenation occurs before or just after the acid gas removal step.

14 Claims, 5 Drawing Sheets

Front-end hydrogenation

METHOD FOR CONTAMINANTS REMOVAL IN THE OLEFIN PRODUCTION PROCESS

BACKGROUND OF THE INVENTION

I. Field of the Invention

The present invention relates to an apparatus and reactor system for recovering polymer grade olefins. Particularly, the invention uses a unique process ordering to remove contaminants that would otherwise prevent the recovery unit from producing polymer grade ethylene and propylene.

II. Background of the Related Art

The mono-olefinic compounds, such as ethylene and propylene, are important commodity petrochemicals useful in a variety of processes for making plastics and other chemical compounds. For instance, ethylene is used to make various polyethylene plastics and chemicals such as vinyl chloride, ethylene oxide, ethylbenzene and alcohol. Propylene is used to make various polypropylene plastics and chemicals such as acrylonitrile and propylene oxide.

Traditionally, the olefins have been produced from petroleum feedstocks at high temperature by steam-cracking, fluid catalytic cracking or deep catalytic cracking processes. See, for example, Hallee et al., U.S. Pat. No. 3,407,789; Woebcke, U.S. Pat. No. 3,820,955, DiNicolantonio, U.S. Pat. No. 4,499,055; Gartside et al., U.S. Pat. No. 4,814,067; Cormier, Jr. et al., U.S. Pat. No. 4,828,679; Rabo et al., U.S. Pat. No. 3,647,682; Rosinski et al., U.S. Pat. No. 3,758,403; Gartside et al., U.S. Pat. No. 4,814,067; Li et al., U.S. Pat. No. 4,980,053; and Yongqing et al., U.S. Pat. No. 5,326,465.

It is also well known in the art that mono-olefinic compounds can be produced from oxygenates, especially alcohols. There are numerous technologies available for producing oxygenates including fermentation or reaction of synthetic gas derived from natural gas, petroleum liquids, carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Syngas production processes are well known and include conventional steam reforming, autothermal reforming or a combination thereof. Methanol, the preferred alcohol for light olefin production, is typically synthesized from the catalytic reaction of hydrogen, carbon monoxide and/or carbon dioxide in a methanol reactor in the presence of a heterogeneous catalyst. For example, in one synthesis process, methanol is produced using a copper/zinc oxide catalyst in a water-cooled tubular methanol reactor. The conventional methanol conversion process is generally referred to as a methanol-to-olefin(s) (MTO) process, where methanol is converted to primarily ethylene and/or propylene in the presence of a molecular sieve catalyst.

Unfortunately, in addition to the mono-olefins obtained by these processes, the produced gases typically contain a large amount of other components such as diolefins, hydrogen, carbon monoxide and paraffins. While, the content of these compounds depends on the severity of the conversion treatment, it is often too low to economically justify their separation and use. Nonetheless, even in low quantities some of these byproducts/contaminants, such as, for example, acetylene and methyl acetylene, must be removed because they act as a poison to the catalysts used for making polymers, e.g., polyethylene, polypropylene, out of the mono-olefinic compounds. Another trace contaminant that may cause a problem in polymer production are oxygenated hydrocarbons (ethers, esters, acids, carbonyls) because the polar nature of the oxygenated hydrocarbons will deactivate the Ziegler-Natta or metallocene polymerization catalysts.

To this end, treating the olefin stream in order to obtain polymer grade ethylene/propylene can take various routes depending on the level of an acetylenic compounds and oxygen present. For instance, plural stage rectification and cryogenic chilling trains have been disclosed, for example in Perry's Chemical Engineering Handbook (5th Edition) and other articles on distillation techniques. Typical rectification units are described in Roberts, U.S. Pat. No. 2,582,068; Rowles et al., U.S. Pat. No. 4,002,042, Rowles et al., U.S. Pat. No. 4,270,940, Rowles et al., U.S. Pat. No. 4,519,825; Rowles et al., U.S. Pat. No. 4,732,598; and Gazzi, U.S. Pat. No. 4,657,571. Especially successful cryogenic operations are disclosed in McCue, Jr. et al., U.S. Pat. No. 4,900,347; McCue, Jr., U.S. Pat. No. 5,035,732; and McCue et al., U.S. Pat. No. 5,414,170.

In a typical hydrogenation reactor, the content of acetylenes in the olefin stream is reduced to below 10 ppm, wherein the acetylenes are converted via (i) catalyst adsorption; (ii) isomerization and (iii) hydrogenation steps to ethane, propane, ethylene or propylene. The process employs hydrogen, which contacts one or more acetylenes under conditions effective to selectively hydrogenate the acetylenes, thereby forming a substantially acetylene-free stream. Preferably, after the hydrogenation of acetylenes, the catalyst does not further hydrogenate the partially hydrogenated product, i.e., ethylene or propylene. For example, the hydrogenation of ethylene and propylene must proceed much more slowly than the partial hydrogenation of acetylenes. Moreover, the partially hydrogenated product can also be protected from subsequent reactions by being rapidly desorbed from the catalyst surface and then not being re-adsorbed again. This thermodynamically dependent selectivity is based on the triple bond being more strongly adsorbed than the corresponding double bond, because of its more electrophilic character. Even relatively small differences in the adsorption energy are sufficient for an acetylenic compound to immediately displace the primary resulting hydrogenation product from the catalyst surface and accordingly act as a retardant for the subsequent reactions.

Conventional hydrogenation processes for the selective hydrogenation of acetylene in the presence of ethylene are typically supported by metals of Group VIII, of which palladium was shown to be the most active and selective metal for the hydrogenation of acetylenes to the corresponding olefins. By-products of the olefin production plant, such as hydrogen sulfide ($H_2S$) and high concentrations of carbon monoxide (CO), typically are removed prior to palladium catalyzed hydrogenation, as these by-products can poison the palladium catalyst. In process configurations where $H_2S$ and CO are still present, use of composites of Group VIII (Co or Ni) and Group VIB (Mo or W) metals in a sulfided state has been proposed, one of which is a cobalt or nickel molybdenum. For example, see U.S. Pat. No. 3,649,525, incorporated herein by reference, wherein a Ni/Mo catalyst was used for desulfurization and hydrogenation of heavy oils. For other examples, numerous references are provided in *Sulphide Catalysts: Their Properties & Applications* by Weisser and Landa (Pergamon Press, 1974), which is incorporated herein by reference. Alternatively, the use of the copper catalysts has also been proposed because it is highly selective to acetylenic hydrogenation. Unfortunately, the activity of copper catalysts is too slow and the catalyst cycle time is undesirably short for the feed streams, which contain higher than about 2000 ppm total alkynes due to fast deactivation caused by the deposition of polymeric material on the catalyst surface.

In a typical conventional separation process, as shown in FIG. 1A, the source such as cracked gas or OTO (oxygenate to olefin) reaction product in a line 101 is compressed in a compressor 201. The compressed gas in line 102 is then caustic washed in the AGR reactor/washer 202 and fed via a line 103 to dryer 203. The dried gas in line 104 is then fed to the chilling unit 205. The liquids from the chilling unit 205 are removed via a line 106.

In the back-end configuration (referring to the placement of the hydrogenation tower), as shown in FIG. 1B, the liquids from line 106 are fed to a demethanizer tower 206. The methane and lighter components are removed from the top of the demethanizer tower 206 via line 108 for further processing. The $C_{2+}$ components are removed from the bottom of the demethanizer tower 206 via line 107 and fed to a deethanizer tower 207. The $C_2$ components are removed from the top of the deethanizer tower 207 in a line 109 and passed to an acetylene hydrogenation reactor 208 for selective hydrogenation of acetylenes and subsequently to a caustic tower 209 to remove $H_2S$ if the sulfide catalyst has been used. The effluent from the hydrogenation reactor 208/optional caustic tower 209 is then fed directly via a line 113 to a $C_2$ splitter 210 for separation of the ethylene from ethane. The ethylene is removed from the top of splitter 210 via $C_2$ heat pump 211 in a line 114 and ethane is removed from the bottom of splitter 210 in a line 115. The $C_{3+}$ components removed from the bottom of the deethanizer tower 207 in a line 110 are directed to a depropanizer tower 212. The $C_3$ components are removed from the top of the depropanizer tower in a line 111 and fed to a $C_3$ hydrogenation reactor 215 to selectively hydrogenate the methyl acetylene and propadiene. If the sulfide catalyst has been used, the effluent from the hydrogenation reactor 215 is passed through a caustic tower 216 and then fed via a line 112 to a $C_3$ splitter 213, wherein the propylene and propane are separated. The propylene is removed from the top of the $C_3$ splitter in a line 116 and the propane is removed from the bottom of the $C_3$ splitter in a line 117. Finally, the $C_{4+}$ components removed from the bottom of the depropanizer tower 212 in a line 118 are directed to a debutanizer 214 for separation into $C_4$ components and $C_{5+}$ gasoline. The $C_4$ components are removed from the top of the debutanizer 214 in a line 119 and the $C_{5+}$ gasoline is removed from the bottom of the debutanizer 214 in a line 120.

In the front-end configuration, as shown in FIG. 1C, the liquids from line 106 are fed to a depropanizer tower 212. The $C_{3-}$ components are removed from the top of the depropanizer tower in a line 111 and fed to a hydrogenation reactor 208 to selectively hydrogenate the acetylene, methyl acetylene and propadiene. If the sulfide catalyst has been used, the effluent from the hydrogenation reactor 208 is passed through a caustic tower 209 and then fed via a line 113 to the demethanizer tower 206. The methane is removed from the top of the demethanizer tower 206 via line 108 for further processing. The $C_2$ and $C_3$ components are removed from the bottom of the demethanizer tower 206 via line 107 and fed to a deethanizer tower 207. The $C_2$ components are removed from the top of the deethanizer tower 207 in a line 109 and passed to a $C_2$ splitter 210 for separation of the ethylene. The ethylene is removed from the top of splitter 210 via $C_2$ heat pump 211 in a line 114, and ethane, removed from the bottom of splitter 210 in a line 115. The $C_3$ components removed from the bottom of the deethanizer tower 207 in a line 110 are directed to a $C_3$ splitter 213, wherein the propylene and propane are separated. The propylene is removed from the top of the $C_3$ splitter in a line 116 and the propane is removed from the bottom of the $C_3$ splitter in a line 117. Finally, the $C_{4+}$ components removed from the bottom of the depropanizer tower 212 in a line 118 are directed to a debutanizer 214 for separation into $C_4$ components and $C_{5+}$ gasoline. The $C_4$ components are removed from the top of the debutanizer 214 in a line 119 and the $C_{5+}$ gasoline is removed from the bottom of the debutanizer 214 in a line 120.

In another permutation of the front-end configuration, the depropanizer tower 212 is placed after the hydrogenation step. Specifically, the liquids from line 106 are fed initially to a hydrogenation reactor 208 to selectively hydrogenate the acetylene, methyl acetylene and propadiene. The effluent from the hydrogenation reactor 208 is then passed through a caustic tower 209 and fed via a line 113 to the rest of the processing/distillation units. This approach is commonly referred to as "raw gas configuration." Commonly, a full-range stream containing both light and heavy components ranging from hydrogen up to $C_5$'s and heavier is processed over a fixed bed of selective hydrogenation catalyst, preferably the partially sulfided nickel catalyst. This catalyst is operated to effect complete removal of simple acetylene and removal of a majority of the methyl acetylene and propadiene. However, about one-half of the butadiene is also hydrogenated. Because these catalysts also promote the hydrogenation of butadiene, they cannot be used when butadiene is in the system unless the $C_4$ stream is first removed. In such instances a depropanizer is generally employed before subjecting the stream to a hydrogenation reaction (front-end process; see FIG. 1C). Furthermore, the use of a raw gas catalytic hydrogenation reactor has not been wide practiced because the position in the flowsheet requires the reactor to fully hydrogenate acetylene, methyl acetylene and propadiene, which all have different rate kinetics. Therefore, subsequent hydrogenation is still required in order to meet product specifications, e.g., the production of the polymer-grade olefin. The present invention solves this impracticality because the raw gas stream in an oxygenate to olefins or MTO process has significantly lower concentrations of acetylene, methyl acetylene and propadiene and makes the raw gas hydrogenation process a viable commercial option.

The front-end reactor configuration of the prior art, however, has its own shortcomings. The process requires multiple beds to reduce temperature rise because the plant experiences operating upsets due to temperature excursions during the initial start up resulting from the sensitivity and activity of the fresh catalyst. Furthermore, the hydrogen to acetylene ratio is uncontrollable. On the other hand, in the "back-end" reactor configuration of the prior art, the process requires an external fluid solvent and must carefully regulate the hydrogen ratio, carbon monoxide content and reactor inlet temperature due to pressure sensitivities to excursions in acetylene and carbon monoxide concentrations. The reactor effluent typically contains less than 1 ppm of acetylene but is contaminated with traces of hydrogen and methane, which also represents a major disadvantage.

Essentially, none of the prior art processes have described a useful method of obtaining relatively high purity olefin components, i.e., polymer grade ethylene and propylene (~99.9% purity), from olefin-containing streams such as an effluent from various types of fluid catalytic cracking reactors in a raw gas catalytic hydrogenation reactor and the effluent from the oxygenate-to-olefin reactors such as the MTO. Therefore, it is desirable to have a useful method of obtaining relatively high purity olefin components from olefin-containing streams that do not have the drawbacks of the systems of the prior art, such as in the use of front-end or back-end hydrogenation systems.

SUMMARY OF THE INVENTION

The present invention provides a method and a system for hydrogenating acetylenes (inclusive of acetylene and methyl acetylene) and removing elemental nitric oxide and oxygen present in the process stream of an olefin production facility. In one particular embodiment of the invention, the process stream is derived from effluent of the petroleum catalytic cracking process and/or the effluent of the oxygenate-to-olefin process in an olefin production plant. In one specific embodiment, the hydrogenation reactor in an olefin production plant is positioned before the caustic tower and before the separation, e.g., distillation steps. Accordingly, in one specific embodiment, the present invention provides a method and a system for hydrogenating the acetylenes and removing nitric oxide and oxygen present in the olefin stream over a sulfided catalyst.

In one embodiment, the present invention provides a method for treating a feedstream comprising butane, butenes, propane, propylene, ethane, ethylene, acetylene, methane, hydrogen, oxygen, nitric oxide, carbon monoxide and mixtures thereof, the method comprising the following steps in sequence: (i) stripping with quench water and compressing the effluent; (ii) hydrogenating the acetylenes selectively in the vapor stream in a mixed phase hydrogenation zone using the sulfided catalyst; (iii) subjecting the stream to acid gas removal; and (iv) separating the polymer-grade olefin components, such as via distillation, dephlegmation and/or absorption processes.

Surprisingly, the present inventors have found that by selectively hydrogenating the acetylene upstream of the caustic tower and subsequent separation means, the caustic tower can be used to provide for removal of carbon dioxide and hydrogen sulfide, while the hydrogenation reactor also reacts nitric oxide and oxygen contaminants. In this manner, the present inventors have found that the number of selective hydrogenation reaction units and acid gas removal units required to fully hydrogenate the acetylene, methyl acetylene, propadiene, butadiene, oxygen and nitrous oxide is reduced. Furthermore, the present inventors have found that sulfided copper and nickel based catalysts can be employed in selectively hydrogenating the acetylene, oxygen and nitrous oxide just upstream or downstream of the caustic tower.

BRIEF DESCRIPTION OF THE DRAWINGS

Various embodiments of the overall invention are shown by way of example in the attached Figures, wherein.

DETAILED DESCRIPTION OF THE INVENTION

The present invention provides a method and reactor system for hydrogenating acetylenes present in the olefin stream derived from the following streams, alone or in combination: petroleum fluid catalytic cracking (FCC) process and oxygenate-to-olefin process in an olefin production plant before distillation steps. According to one specific embodiment of the invention, the stream from the oxygenate-to-olefin reactor is used. According to another specific embodiment of the invention, the oxygenate-to-olefin reactor is the methanol-to-olefin (MTO) reactor.

Figure 1A:
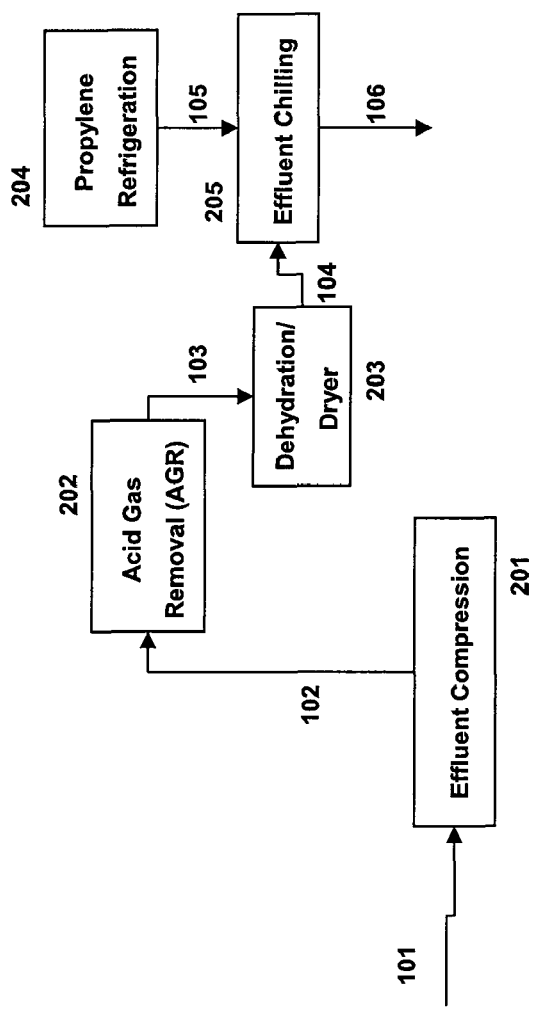
FIG. 1A is a flow diagram showing the initial stages of a process for separating olefin in an olefin production plant of the prior art.
Figure 1B:
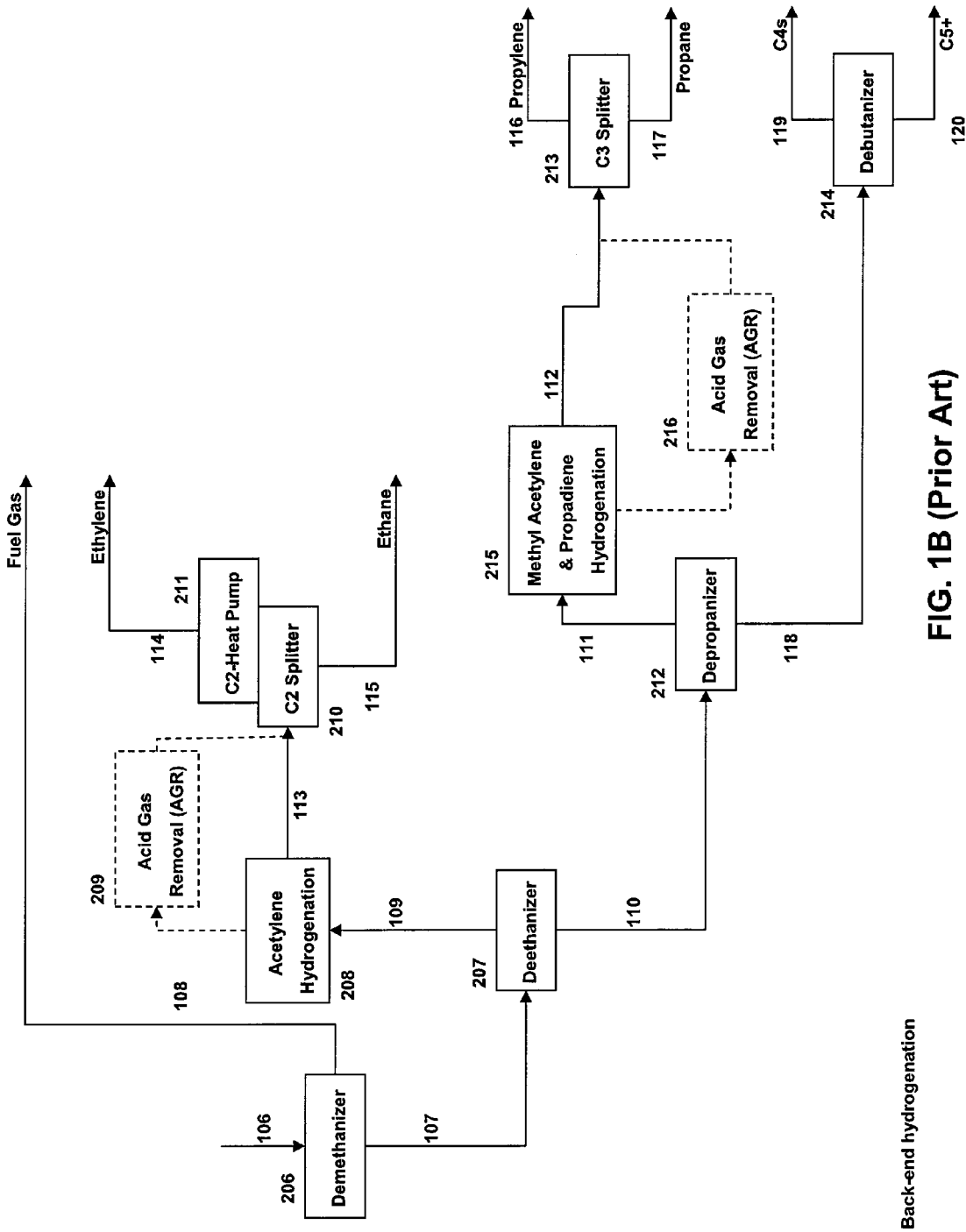
FIG. 1B is a flow diagram showing a second part of a process for separating olefin in an olefin production plant of the prior art having a back-end configuration.
Figure 1C:
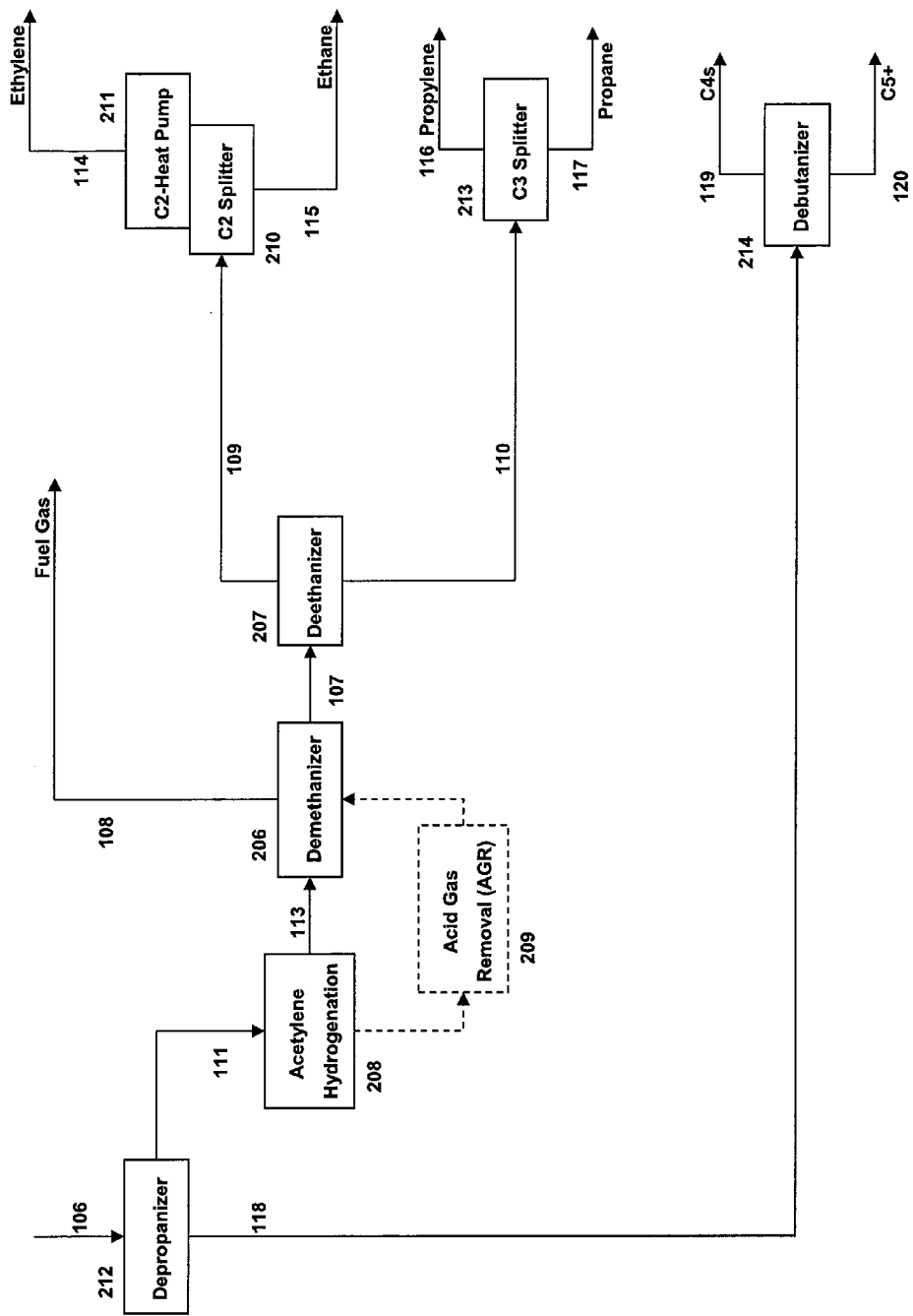
FIG. 1C is a flow diagram showing a second part of a process for separating olefin in an olefin production plant of the prior art having a front-end configuration.
Figure 2:
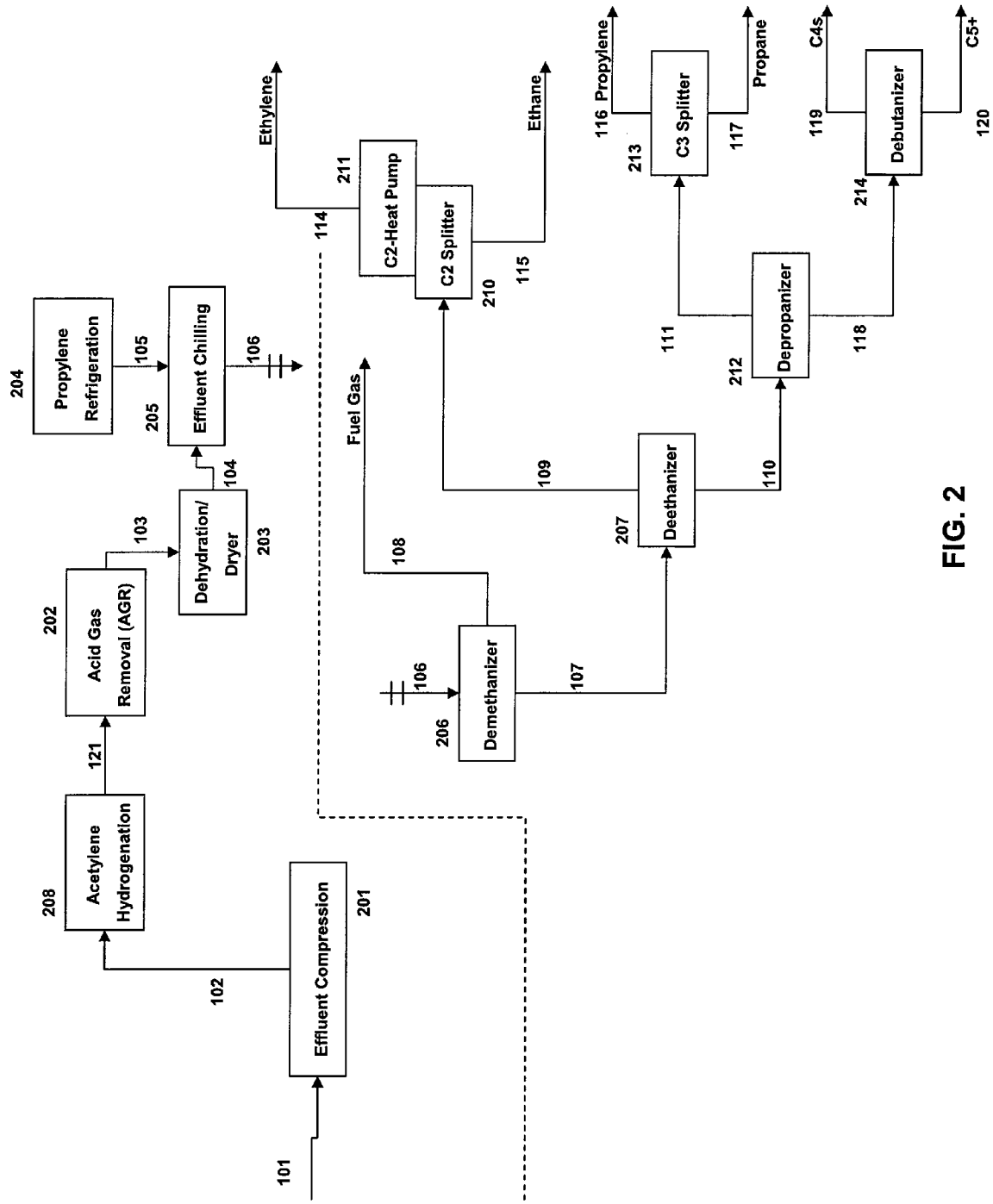
FIG. 2 is a flow diagram showing a process for removing acetylenes from the olefin containing stream in an olefin production plant of the present invention.
Figure 3:
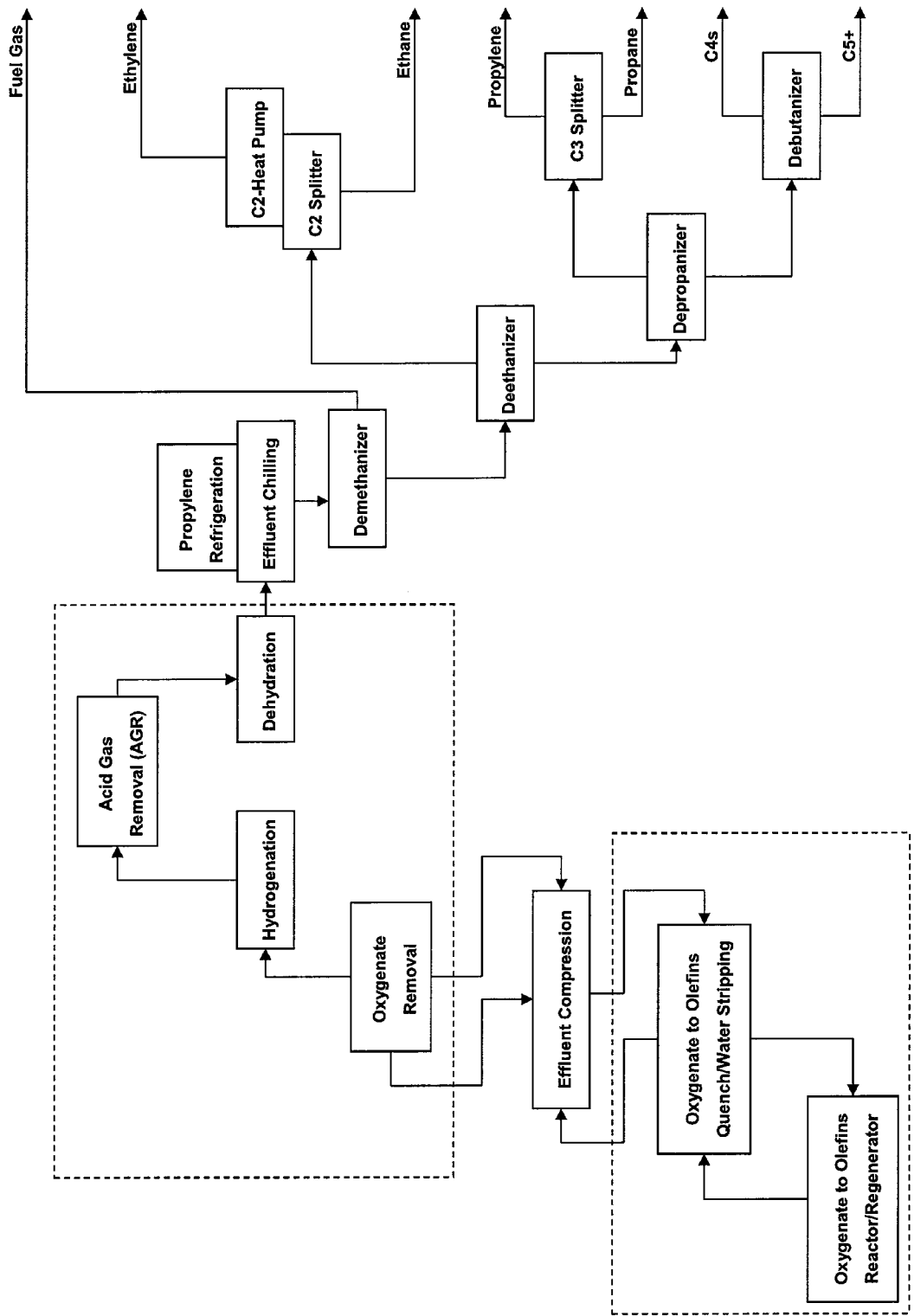
FIG. 3 is a flow diagram showing an exemplary embodiment of the present invention applied to an MTO process.

In one specific embodiment of the present invention, as shown in FIG. 2, the source such as, for example, the MTO reaction product in a line 101 is compressed in a compressor 201, preferably a multi-stage compressor with two or three stages. In this invention, the contaminants, particularly including acetylenes, are removed from the provided olefin stream at low pressure. An advantage of using a low pressure separation is that lower temperatures would allow for fewer equipment fouling problems and would require compressors with fewer stages of compression. In addition, such a process will use less energy to run associated operating equipment, such as reboilers and condensers.

Normally, the product effluent from an MTO reactor contains one or more olefins, e.g., acetylene, methyl acetylene, ethylene, propylene, 1-butene, 2-butene, isobutene, butadiene, $C_5$ olefins, $C_5$ diolefins, $C_6$ olefins and $C_{7+}$ olefins. In accordance with the present invention, the acetylenes-containing stream preferably is selected from the bottoms stream from a quench tower or the bottom stream from a water absorption unit. These streams, alone or in combination, can contain from 0.2 to 1.0 volume percent of acetylene, 0 to 0.2 volume percent of methyl acetylene, and 0 to 1.0 volume percent of ethyl acetylene. The ranges provided are on a dry basis, i.e., water stripped.

The compressed gas in line 102 is then passed to a hydrogenation reactor 208 for selective hydrogenation of acetylenes, wherein the acetylenes are hydrogenated over a catalyst, such as, a sulfided copper or nickel catalyst. While, a sulfided copper and/or nickel catalyst is used in the hydrogenation unit in accordance with the present invention, any other hydrogenation catalyst could be implemented in accordance with the present invention. Suitable metal sulfides which may be used as catalysts in the process of the present invention include, for example sulfides of zinc, copper, gallium, cadmium, chromium, molybdenum, tungsten, cobalt, nickel, ruthenium and iron and mixtures thereof. According to a specific embodiment of the invention, the catalyst is copper sulfide, either alone or in combination with at least one other metal sulfide, for example molybdenum or tungsten sulfide. Examples of suitable catalysts include a sulfided nickel-molybdenum. The catalyst impregnation in, for example, the silica or alumina support with or without a promoter metal is well known in the art. For examples of catalyst impregnation, numerous references are provided in *Catalyst Preparation: Science and Engineering* edited by Regalbuto (CRC Press, 2007), which is incorporated herein by reference. According to one specific embodiment of the invention, the olefin stream is passed with an excess of hydrogen or hydrogen rich gas over a hydrogenation catalyst. The catalyst, e.g., a sulfided copper or sulfided nickel catalyst, is impregnated on an alumina or silica support.

According to an embodiment of the invention, the hydrogenation process occurs in a fixed bed downflow reactor operating at greater than about 25 bar g and according to another embodiment from about 15 and about 30 bar g and at a temperature range of about 150 to 280° C. Under optimized conditions, acetylenes are converted to alkenes and/or paraffins.

The effluent from the hydrogenation reactor 208 is then fed via a line 121 to the acid gas removal (AGR) reactor/washer 202 and subsequently fed via a line 103 to dryer 203.

In one embodiment, the olefin stream is treated to remove entrained acid gases such as $CO_2$ and $H_2S$. Solid or liquid acid gas treatment systems can be used in this invention. In either system, the acid gas is removed from the olefin stream by contacting the effluent with an acid gas absorbent or adsorbent. Examples of such absorbents or adsorbents include amines, potassium carbonate, caustic, alumina, molecular sieves and membranes, particularly membranes formed of polysulfone, polyimid, polyamide, glassy polymer and cellulose acetate. Solutions containing amines and caustic compounds are preferred, with caustic compounds being more preferred. Caustic compounds suitable for use in the present invention include alkaline compounds, which are effective in removing acid gas from an olefin stream. Examples of such alkaline compounds include, but are not limited to, sodium hydroxide and potassium hydroxide.

Following acid gas treating, it may be desirable to remove additionally entrained water by drying the AGR treated olefin stream. According to one embodiment of the invention, a desiccant drying system can be used to remove water. It is desirable in the process of the invention to provide an olefin stream that is substantially dry to prevent formation of ice of hydrates in the subsequent cryogenic distillation recovery system.

The dried gas in line 104 is then fed to the chilling unit 205. The liquids from the chilling unit 205 are removed via a line 106.

Various distillation steps may be envisioned subsequent to the effluent chilling in unit 205, which are well known in the art. In one embodiment of the invention, the liquids from line 106 are fed to a demethanizer tower 206. The methane is removed from the top of the demethanizer tower 206 via line 108 for further processing. The $C_{2+}$ components are removed from the bottom of the demethanizer tower 206 via line 107 and fed to a deethanizer tower 207. The $C_2$ components are removed from the top of the deethanizer tower 207 in a line 109 and passed to a $C_2$ splitter 210 for separation of the ethylene. The ethylene is removed from the top of splitter 210 via $C_2$ heat pump 211 in a line 114, and ethane, removed from the bottom of splitter 210 in a line 115. The $C_{3+}$ components removed from the bottom of the deethanizer tower 207 in a line 110 are directed to a depropanizer tower 212. The $C_3$ components are removed from the top of the depropanizer tower in a line 111 and fed to a $C_3$ splitter 213, wherein the propylene and propane are separated. The propylene is removed from the top of the $C_3$ splitter in a line 116 and the propane is removed from the bottom of the $C_3$ splitter in a line 117. Finally, the $C_{4+}$ components removed from the bottom of the depropanizer tower 212 in a line 118 are directed to a debutanizer 214 for separation into $C_4$ components and $C_{5+}$ gasoline. The $C_4$ components are removed from the top of the debutanizer 214 in a line 119 and the $C_{5+}$ gasoline is removed from the bottom of the debutanizer 214 in a line 120.

It will be appreciated by persons skilled in the art that the present invention is not limited to what has been particularly shown and described hereinabove. Rather, the scope of the present invention is defined by the claims which follow. It should further be understood that the above description is only representative of illustrative examples of embodiments. For the reader's convenience, the above description has focused on a representative sample of possible embodiments, a sample that teaches the principles of the present invention. Other embodiments may result from a different combination of portions of different embodiments.

The description has not attempted to exhaustively enumerate all possible variations. The alternate embodiments may not have been presented for a specific portion of the invention, and may result from a different combination of described portions, or that other undescribed alternate embodiments may be available for a portion, is not to be considered a disclaimer of those alternate embodiments. It will be appreciated that many of those undescribed embodiments are within the literal scope of the following claims, and others are equivalent. Furthermore, all references, publications, U.S. patents, and U.S. patent application Publications cited throughout this specification are hereby incorporated by reference as if fully set forth in this specification.

What is claimed is:

1. A method for hydrogenating acetylenes in an olefin producing process, said method comprising:
   (a) stripping an olefin containing hydrocarbon effluent derived from said process in a water stripping tower and a compressor to remove water from the effluent and to condense said effluent;
   (b) removing oxygenates from said condensed effluent of step (a) to remove unreacted oxygenates from said effluent;
   (c) hydrogenating the effluent of step (b) by selectively hydrogenating at least a portion of acetylene, oxygen and nitrous oxides;
   (d) subjecting the effluent of step (c) to a caustic tower/reactor to remove hydrogen sulfide and carbon dioxide;
   (e) dehydrating the effluent of step (d) and subjecting said effluent to a chilling train to cool and at least partially condense said effluent; and
   (f) separating the product of step (e) in a downstream separation zone.

2. The method as defined in claim 1, wherein said downstream separation zone comprises a demethanizer, a deethanizer, a depropanizer, a debutanizer or a combination thereof.

3. The method as defined in claim 1, wherein the olefin containing effluent of step (a) comprises butane, butenes, propane, propylene, ethane, ethylene, acetylene, methane, hydrogen, carbon monoxide, methyl acetylene, butadiene, nitric oxide, oxygen and mixtures thereof.

4. The method defined in claim 1, wherein the olefin containing effluent of step (a) comprises alone or in combination from about 0.2 to about 1.0 volume percent acetylene, from about 0 to about 0.2 volume percent methyl acetylene, and from about 0 to about 1.0 volume percent ethyl acetylene.

5. The method as defined in claim 1, wherein the hydrogenation is performed at a temperature of from about 150° C. to about 280° C. and a pressure of from about 15 bar g to about 30 bar g over a sulfided hydrogenation catalyst.

6. The method as defined in claim 5, wherein said sulfided hydrogenation catalyst comprises a copper sulfide.

7. The method as defined in claim 5, wherein said sulfided hydrogenation catalyst comprises a nickel sulfide.

8. The method as defined in claim 1, wherein the olefin producing process is a hydrocarbon catalytic cracking process.

9. The method as defined in claim 8, wherein the hydrocarbon catalytic cracking process is a deep catalytic cracking process.

10. The method as defined in claim 8, wherein the hydrocarbon catalytic cracking process is a fluid catalytic cracking process.

11. The method as defined in claim 1, wherein the olefin producing process is an oxygenate-to-olefin process.

12. The method as defined in claim 11, wherein the oxygenate-to-olefin process is a methanol-to-olefin (MTO) process.

13. The method as defined in claim 1, wherein the product of step (f) is a polymer-grade olefin.

14. The method defined in claim 13, wherein the polymer grade olefin contains less then 5 parts per million (ppm) of contaminants.

* * * * *